United States Patent [19]

Shih

[11] Patent Number: 5,037,930

[45] Date of Patent: Aug. 6, 1991

[54] HETEROCYCLIC QUATERNIZED NITROGEN-CONTAINING CELLULOSIC GRAFT POLYMERS

[75] Inventor: Jenn S. Shih, Paramus, N.J.

[73] Assignee: GAF Chemicals Corporation, Wayne, N.J.

[21] Appl. No.: 411,081

[22] Filed: Sep. 22, 1989

[51] Int. Cl.$^5$ .............................................. C08G 18/00
[52] U.S. Cl. .................................. 527/301; 527/312; 527/313; 527/314; 527/315
[58] Field of Search ............... 527/300, 301, 312, 313, 527/314, 315

[56] References Cited

U.S. PATENT DOCUMENTS 4,831,097  5/1989  Chuang et al. ...................... 514/846

Primary Examiner—Nathan M. Nutter
Attorney, Agent, or Firm—Walter Katz; Marilyn J. Maue; Joshua J. Ward

[57] ABSTRACT

In this invention, at least two monomers are grafted onto hydroxy-containing cellulose polymer. The invention thus provides a polymer of a cellulose containing a hydroxy group on which is grafted, by replacement of the hydrogen atom of the hydroxy group, with a copolymer having a polymerized lactam-containing moiety and a polymerized quaternized ammonium-containing moiety. The ratio of the polymerized lactam group of the quaternized ammonium moiety in the grafted copolymer can be predetermined to provide polymers which are particularly useful in the hair treatment industry.

14 Claims, No Drawings

HETEROCYCLIC QUATERNIZED NITROGEN-CONTAINING CELLULOSIC GRAFT POLYMERS

BACKGROUND OF THE INVENTION

1. Field of the Invention

This invention relates to heterocyclic quaternized nitrogen-containing cellulosic graft polymers and methods for their preparation. In another aspect the invention relates to the use of said polymers in skin and hair treating formulations.

2. Description of the Prior Art

Quaternized nitrogen-containing cellulose ether derivatives are well known and possess certain desirable properties. U.S. Pat. No. 3,47z,840 describes their substantivity to many substrates. However, these quaternized compounds are strongly polar and lack lipophilic groups. Thus they are of limited use in compositions which are relatively incompatible with polar anionic polymers.

High charge density N,N-dialkenyl-N, N-dialkyl ammonium halide cellulosic graft polymers are disclosed in U.S. Pat. No. 4,464,523 and hydrophobe substituted, quaternary nitrogen-containing cellulose ether derivatives are the subject of U.S. Pat. No. 4,663,159. However, when employed in hair care, these polymers are not easily removed by shampoos and they tend to build up on the hair filaments giving a dull waxy appearance. On the other hand, the non-ionic cellulose ethers of U.S. Pat. No. 4,228,277 possess little substantivity in that they do not interact with ionic substrates such as the keratinous material of hair and skin.

An improved grafting monomer which contains both pyrrolidone and ammonium moieties is 2-methacryloxyloxyethyl[(1-pyrrolidonyl) methyl]ammonium chloride (MEPDAC) having the formula:

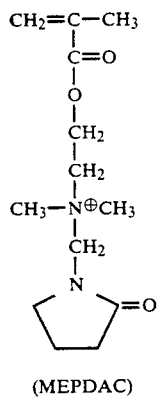

(MEPDAC)

U.S. Pat. No. 4,831,097 discloses such water soluble heterocyclic cationic graft polymers of cellulose containing both pyrrolidone and quaternary ammonium moieties grafted onto hydroxyethyl cellulose. This polymer was used as an antistat and conditioner in hair and/or skin preparations. The quaternary ammonium groups gave the product substantivity, but too many such groups made it difficult to remove from the hair by washing, resulting in build-up. On the other hand, increasing the number of pyrrolidone groups gave the product better compatability properties, permitting easier combing. However, this grafting monomer has only an equal number of pyrrolidone and quaternary ammonium moieties, which limit the effectiveness of the grafting.

Accordingly, it is an object of the present invention to provide polymers in which the ratio of pyrrolidone to quaternary ammonium groups in the grafting monomer can be predetermined to accommodate the particular hair product use intended for the graft polymer.

Another object of this invention to overcome the above deficiencies and to provide a substantive, mildly cationic cellulosic graft polymer particularly suitable for conditioning and cleansing of hair and skin and useful in all applications in which related quaternary nitrogen-containing cellulosic materials have been utilized previously.

These and other objects and features of the invention will become apparent from the following description and disclosure.

SUMMARY OF THE INVENTION

In this invention, at least two monomers are grafted onto hydroxy-containing cellulose polymer. The invention thus provides a polymer of a cellulose containing a hydroxy group on which is grafted, by replacement of the hydrogen atom of the hydroxy group, with a copolymer having a polymerized lactam-containing moiety and a polymerized quaternized ammonium-containing moiety. The ratio of the polymerized lactam group to the quaternized ammonium moiety in the grafted copolymer can be predetermined to provide polymers which are particularly useful in the hair treatment industry.

The grafted cellulosic polymer product of the invention is also less susceptible to water hydrolysis, and is more water soluble, than the corresponding polymer grafted with a single monomer (U.S. No. 4,831,097) in which the ratio of lactam to quaternized ammonium groups is fixed at 1:1.

DETAILED DESCRIPTION OF THE INVENTION

The lactam-containing moiety of the polymers herein has the formula:

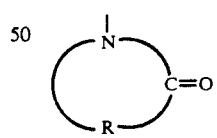

where R is a $C_3$-$C_8$ alkylene group which is optionally substituted with methyl. The monomer reactants to provide such lactam moiety is a lactam group connected to a polymerizable group, such as vinyl, acrylate or acryklamide to provide monomers having the formulas:

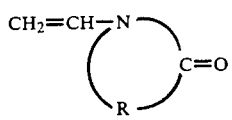

-continued

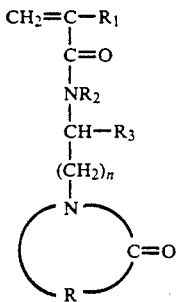

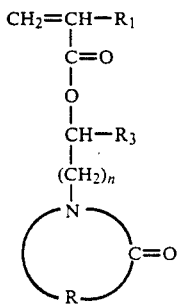

where $R_1$ is hydrogen or $C_1$-$C_4$ alkyl, $R_2$ is hydrogen or $C_1$-$C_3$ alkyl, $R_3$ is hydrogen or $C_1$-$C_4$ alkyl, and n is 0-4.

A preferred lactam compound is N-[1-(2-pyrrolidonyl) ethyl] methyacrylamide (PEAA) having the formula:

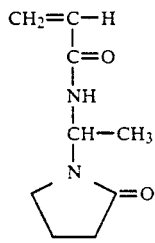

(PEAA)

Other suitable lactam-containing monomers for use herein include the following compounds: vinyl pyrrolidone, and pyrrolidonyl ethyl acrylate and methacrylate.

The quaternized ammonium moiety in the grafted polymers of the invention are made from monomers which are already quaternized, or a are quaternized after post-polymerization, e.g. with an alkyl-halide or sulfate. The resultant quaternized moiety in the polymer has the formula:

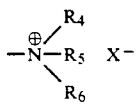

where $R_4$, $R_5$ and $R_6$ are independently alkayl $C_1$-$C_8$, and X is an anion, such as chloride or sulfate.

This moiety is connected to a polymerizable acrylate or acrylamide group, where $R_1$, $R_2$, $R_3$ and n are independent of their embodiments in the lactam-containing moiety, as follows:

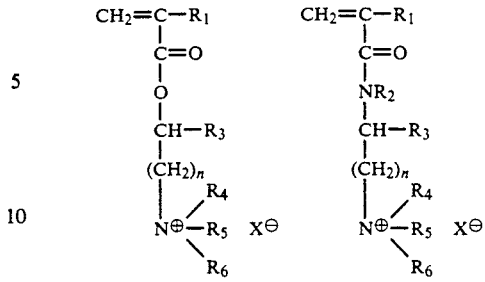

A preferred quaternized ammonium moiety in the compounds herein is methylacrylamidopropyl trimethyl ammonium chloride (MAPTAC) having the formula:

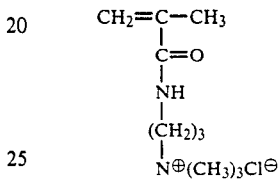

(MAPTAC)

The cellulosic residue is derived from cellulose compounds including $C_1$ to $C_4$ alkylated cellulose, hydroxy $C_2$ to $C_3$ alkyl cellulose, carboxy $C_1$ to $C_2$ alkyl cellulose, hydroxy $C_2$ to $C_3$ alkyl methyl cellulose and hydroxyethyl carboxymethyl cellulose. These cellulosic polymers are water soluble and contain 50 to 20,000 anhydroglucose units. Preferred of this group are cellulose derivatives having the structure:

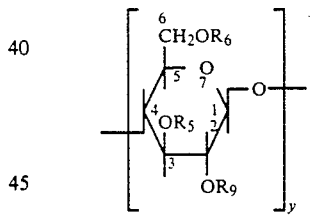

wherein y has a value of from 50 to 20,000, preferably from 200 to 8,000, and $R_5$, $R_6$ and $R_9$ are each hydrogen, hydroxy/ lower alkyl, lower hydroxyalkyl, lower alkoxyalkyl, carboxymethyl or carboxymethyl lower hydroxyalkyl. Although grafting onto the cellulose polymers can take place at any one or more of the hydroxy groups at 2, 3 and 6 positions of the anhydroglucose unit, it is preferred that not more than one graft per anhydroglucose unit be present in the product and while grafting along the anhydroglucose backbone can be randomly distributed among positions 2, 3 and 6, most often the comonomeric moiety attaches to the 6th position.

The polymers of the invention thus have the general formula:

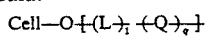

where Cell is a cellulosic residue, L is a lactam moiety and Q is a quaternized ammonium moiety. The subscripts 1 and q refer to the molar amounts of L and Q, respectively, in the LQ copolymer.

Suitably the l/q ratio can be predetermined by the relative amounts of monomers used to form the polymer; accordingly, the l/q ratio can vary from 1:99 to 99:1, preferably about 1:2 to 10:1, and most preferably about 2:1 to 4:1.

The weight ratio of cellulose to copolymer of L and Q suitably is about 1:2 to 1:10 and preferably about 4 to 1:6.

In the process for synthesizing the graft copolymer of this invention, the cellulosic polymer, the lactam and unquaternized or quaternized monomrer are swelled in a suitable solvent, conveniently an aqueous solution of an inert, water-miscible solvent such as acetone, isopropanol, methyl ethyl ketone, etc., and are stirred for a period of from about 0.5 to about 8 hours. A peroxide free radical initiator in aqueous solution is then stirred into the solution. A ferrous salt activator is also added and reaction ensues. A second portion of the peroxide also may be added if desired. The mixture then is reacted over a period of from about 2 to about 10 hours at a temperature within the range of from about 0° to about 80° C., preferably between about 20° and about 30° C. The reaction product is then separated from the supernate by filtration and is washed with a suitable liquid, such as for example, acetone, isopropanol, methyl ethyl ketone, etc. and, if necessary, the pH is adjusted to between about 5.5 and about 8 with a conventional base; although usually no adjustment is necessary since the products normally have a pH of about 5.8 to about 6.8. The product is recovered by filtration or any other convenient means and dried.

Suitable redox free radical initiators for the above reaction include a peroxide such as hydrogen peroxide, t-butyl hydroperoxide, employed with a ferrous salt activator such as ferrous citrate, ferrous chloride, ferrous gluconate, ferrous nitrate, ferrous sulfate heptahydrate, ferrous ammonium sulfate hexahydrate, ferrous ethylene diaminetetraacetic acid complex, etc. These ferrous salts are employed with peroxide in a concentration of between about 0.01 and about 0.2 mole % based on peroxide. A ceric ammonium nitrate in one normal nitric acid may also be employed as the initiator in place of the redox free radical initiators.

As indicated previously, the copolymers are present in the form of their quaternary salts. Quaternization of the copolymer may take place before or after polymerization. When quaternization is carried out after polymerization, the grafted product is subjected to a treatment conductive to quaternization of the tertiary amino group, utilizing a conventional quaternizing agent. Thus, noting the above structural formula for the copolymers, suitable quaternizing agents include, such as, dialkyl sulfates, e.g., dimethyl sulfate, diethyl sulfate, etc.; alkyl sulfonic acid, e.g., methyl sulfonic acid, ethyl sulfonic acid, etc.; benzyl halides, e.g., benzyl chloride, benzyl bromide, benzyl iodide, etc.; alkyl halide, etc.

The invention will be described more fully by reference to the following examples.

EXAMPLE 1

Preparation of Hydroxmethyl Cellulose (HEC) Grafted with PEAA and MAPTAC

A 1-liter resin kettle equipped with an anchor agitator, condenser, nitrogen inlet tube and thermometer was charged with 57.4 g of hydroxyethyl cellulose, 4.12 g (0.0226 mole) of N-[1-(2-pyrrolidonyl) ethyl]acrylamide (PEAA) and 10.0 g (0.0226 mole) of a 50% active aqueous solution of methacrylamido propyl trimethyl ammonium chloride (MAPTAC) in 188 g of an acetone/water (170 g/18 g) mixture. The reaction solution was stirred for 16 hrs. at 25° C. while nitrogen was bubbled in at a rate of 50 ml/min. Acetone was added as needed to keep the liquid level constant. Then 1.81 g of 30% hydrogen peroxide was added. After 5 minutes, a solution of 0.148 g of ethylene diamine tartaric acid disodium salt dihydrate dissolved in 4.0 ml of distilled water to which was added 0.15% g of ferrous ammonium sulfate was poured into the reaction kettle. Then 5 minutes later, 0.907 g of a 30% hydrogen peroxide solution was added and the reaction mixture was stirred overnight (16 hrs.) at 25° C. Then 100 g of acetone was added over 2 minutes to restore the liquid level. The solution then was stirred for another 30 minutes. Agitation and the nitrogen flow then was discontinued. The resultant polymer (98%) was filtered, washed with acetone and dried in an oven at 80° C.

EXAMPLE 2

Preparation of HEC Grafted with Pyrrolidonylethylacrylate (PEA) and MAPTAC

A 1-liter resin kettle equipped with an anchor agitator, condenser, nitrogen inlet tube and thermometer was charged with 57.4 g of hydroxyethyl cellulose, 4.12 g (0.0226 mole) of N-[2-(2-pyrrolidonyl) ethyl]acrylamide and 10.0 g (0.0226 mole) of a 50% active aqueous solution of methacrylamido propyl trimethyl ammonium chloride (MAPTAC) in 188 g of an acetone/water (170 g/18 g) mixture. The reaction solution was stirred for 16 hrs. at 25° C. while nitrogen was bubbled in at a rate of 50 ml/min. Acetone was added as needed to keep the liquid level constant. Then 1.81 g of 30% hydrogen peroxide was added. After 5 minutes, a solution of 0.148 g of ethylene diamine tartaric acid disodium salt dihydrate dissolved in 4.0 ml of distilled water to which was added 0.15% g of ferrous ammonium sulfate was poured into the reaction kettle. Then 5 minutes later, 0.907 g of a 30% hydrogen peroxide solution was added and the reaction mixture was stirred overnight (16 hrs.) at 25° C. Then 100 g of acetone was added over 2 minutes to restore the liquid level. The solution then was stirred for another 30 minutes.

Agitation and the nitrogen flow then were discontinued. The resultant polymer was filtered, washed with acetone and dried in an oven at 80° C.

EXAMPLE 3

Preparation of HEC Grafted with PEAA and Dimethylaminoethyl Methacrylate (DMAEMA) and Post-Quaternized A 1-liter resin kettle equipped with an anchor agitator, condenser nitrogen inlet tube and thermometer was charged with 57.4 g of hydroxyethyl cellulose, 4.12 g (0.0226 mole) of (1-pyrrolidonyl) ethyl-1-acrylamide (PEAA) and 10.0 g (0.0226 mole) of a 50% active aqueous solution of dimethylamino ethyl methacrylate (DMAEMA) in 188 g of an acetone/water (170 g/18 g) mixture. The reaction solution was stirred for 16 hrs. at 25° C. while nitrogen was bubbled in at a rate of 50 ml/min. Acetone was added as needed to keep the liquid level constant. Then 1.81g of 30% hydrogen peroxide was added. After 5 minutes, a solution of 0.148 g of ethylene diamine tartaric acid disodium salt dihydrate dissolved in 4.0 ml of distilled water to which was added 0.5% g of ferrous ammonium sulfate was poured into the reaction kettle. Then 5 minutes later, 0.907 g of a 30% hydrogen peroxide solution was added and the reaction mixture was stirred overnight (16 hrs.) at 25° C. 2.85 g of diethyl sulfate was charged. Then 100 g of acetone was added over 2 minutes to restore the liquid level. The solution then was stirred for another 30 minutes. Agitation and the nitrogen flow then were discontinued. The resultant polymer was filtered, washed with acetone and dried in an oven at 80° C.

EXAMPLE 4

Preparation of HEC Grafted with Vinyl Pyrrolidone (VP) and MAPTAC

A 1-liter resin kettle equipped with an anchor agitator, condenser nitrogen inlet tube and thermometer was charged with 57.4 g of hydroxyethyl cellulose, 2.51 g (0.0226 mole) of vinyl pyrrolidone and 10.0 g (0.0226 mole) of a 50% mathacrylamido propyl trimethyl ammonium chloride (MAPTAC) in 188 g of an acetone/water (170 g/18 g) mixture. The reaction solution was stirred for 16 hrs. at 25° C. while nitrogen was bubbled in at a rate of 50 ml/min. Acetone was added as needed to keep the liquid level constant. Then 188g of 30% hydrogen peroxide was added. After 5 minutes, a solution of 0.148 g of ethylene diamine tartaric acid disodium salt dihydrate dissolved in 4.0 ml of distilled water to which was added 0.15% g of ferrous ammonium sulfate was poured into the reaction kettle. Then 5 minutes later, 0.907 g of a 30% hydrogen peroxide solution was added and the reaction mixture was stirred overnight (16 hrs.) at 25° C. Then 100 g of acetone was added over 2 minutes to restore the liquid level. The solution then was stirred for another 30 minutes. Agitation and the nitrogen flow then were discontinued. The resultant polymer was filtered, washed with acetone and dried in an oven at 80° C.

EXAMPLE 5

Preparation of HEC Grafted with PEAA and Quaternized DMAEMA

A 1-liter resin kettle equipped with an anchor agitator, condenser nitrogen inlet tube and thermometer was charged with 57.4 g of hydroxyethyl cellulose, 4.12 g (0.0226 mole) of (1-pyrrolidonyl) ethyl-1-acrylamide (PEAA) and 9.5 g (0.0226 mole) of a 50% methacryloxy ethyl trimethyl ammonium chloride (MOETAC) in 188 g of an acetone/water (170 g/18 g) mixture. The reaction solution was stirred for 16 hrs. at 25° C. while nitrogen was bubbled in at a rate of 50 ml/min. Acetone was added as needed to keep the liquid level constant. Then 1.81 g of 30% hydrogen peroxide was added. After 5 minutes, a solution of 0.48 g of ethylene diamine tartaric acid disodium salt dihydrate dissolved in 4.0 ml of distilled water to which was added 0.15% g of ferrous ammonium sulfate was poured into the reaction kettle. Then 5 minutes later, 0.907 g of a 30% hydrogen peroxide solution was added and the reaction mixture was stirred overnight (16 hrs.) at 25° C. Then 100 g of acetone was added over 2 minutes to restore the liquid level. The solution then was stirred for another 30 minutes. Agitation and the nitrogen flow then were discontinued. The resultant polymer was filtered, washed with acetone and dried in an oven at 80° C.

In accordance with the present invention, a copolymer of a lactam monomer and a quaternized ammonium monomer is grafted onto a hydroxy containing cellulose in a predetermined ratio, so that, independently, the desired number of lactam and ammonium groups are present in the polymer. In particular, the desired excess of lactam groups for comb smoothness in hair preparation application, and a minimum of quaternized ammonium groups, for conditioning, can be provided in this invention.

While the invention has been described with particular reference to certain embodiments thereof, it will be understood that changes and modifications may be made which are within the skill of the art. Accordingly, it is intended to be limited by the appended claims only, in which:

What is claimed is:

1. A cellulosci graft polymer containing cellulose units having at least one hydroxy group therein on which is grafted, by replacement of the hydrogen atom of said at least one hydroxy group, with a copolymer having a plymzerized lactam-containing moiety and a polymerized quaternized ammonium-containing moiety.

2. A cellulosic graft polymer containing cellulose units having the formula:

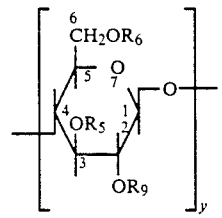

wherein $R_5$, $R_6$ and $R_9$ are selected from hydrogen, lower alkyl, lower hydroxyalkyl, lower alkoxyalkyl, carboxymethyl and carboxymethyl lower hydroxyalkyl, wherein at least one of $R_5$, $R_6$ and $R_9$ is hydrogen which is replaced by at least a polymerizable lactam-containing moiety and a polymerizable quaternized ammonium-containing moiety.

3. A cellulosic graft polymer according to claim 1, wherein the mole ratio of polymerized lactam-containing moiety to quaternized ammonium-containing moiety is about 1:99 to 99:1, preferably about 1:2 to 10:1, and most preferably about 2:1 to 4:1, and the wt. ratio of cellulose to a total of said lactam and quaternized moieties is about 1:2 to 1:10.

4. A cellulosic graft polymer according to claim 3 wherein said wt. ratio is about 1:4 to 1:6.

5. The polymer according to claim 1 wherein the lactam-containing moiety has the formula:

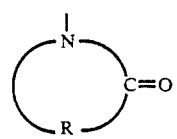

where R is a $C_3$-$C_8$ alkylene group.

6. The polymer according to claim 5 wherein the lactam-containing moiety is derived from a monomer having the formula:

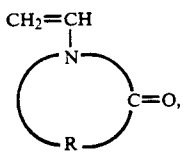

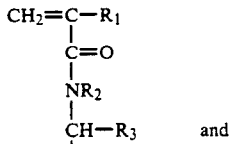 and

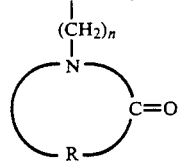

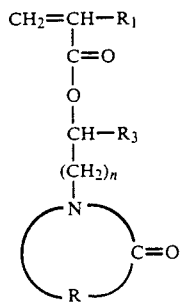

where $R_1$ is hydrogen or $C_1$-$C_4$ alkyl, $R_2$ is hydrogen or $C_1$-$C_3$ alkyl, $R_3$ is hydrogen or $C_1$-$C_4$ alkyl, and n is 0-4.

7. The polymer according to claim 6 wherein the lactam monomer is N-[1-(2-pyrrolidonyl)ethyl]methacrylamide.

8. The polymer according to claim 2 wherein the quaternized ammonium moiety has the formula:

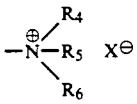

where $R_4$, $R_5$ and $R_6$ are independently alkyl $C_1$-$C_8$, and X is an anion.

9. The polymer according to claim 8 wherein the quaternized ammonium moiety is derived from a monomer having the formula:

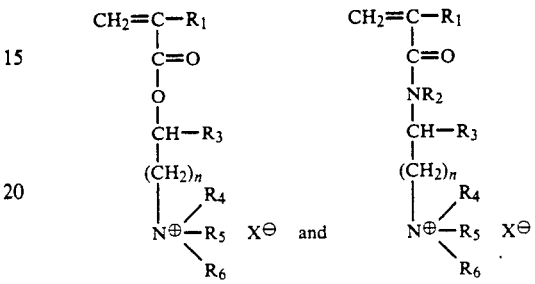

where $R_1$, $R_3$, $R_4$, $R_5$, $R_6$ and n are as defined above.

10. The polymer according to claim 9 wherein the quaternized ammonium moiety is derived from methylacrylamidopropyl trimethyl ammonium chloride.

11. A cellulosic graft polymer having the general formula:

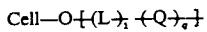

where Cell is a cellulosic residue, L is a lactam moiety and Q is a quaternized ammonium moiety.

12. A cellulosic graft polymer according to claim 11 wherein the l/q ratio is 1:909 to 99:1.

13. A cellulosic graft polymer according to claim 11 wherein the l/q ratio is about 1:2 to 10:1.

14. A cellulosic graft polymer according to claim 11 wherein l/q is about 2:1 to 4:1.

* * * * *